United States Patent
Cheuk et al.

(10) Patent No.: US 8,901,292 B2
(45) Date of Patent: Dec. 2, 2014

(54) METHOD OF MASS PRODUCTION OF TETRAKIS(P-NITROPHENYL)PORPHYRINS

(75) Inventors: Kevin Ka Leung Cheuk, Hong Kong (CN); John Haozhong Xin, Hong Kong (CN); Priscilla Pui Sze Lee, Hong Kong (CN); Zhi Xue, Hong Kong (CN)

(73) Assignee: The Hong Kong Polytechnic Univeristy, Hung Hom, Kowloon, Hong Kong (HK)

( * ) Notice: Subject to any disclaimer, the term of this patent is extended or adjusted under 35 U.S.C. 154(b) by 50 days.

(21) Appl. No.: 13/354,352

(22) Filed: Jan. 20, 2012

(65) Prior Publication Data

US 2013/0190486 A1    Jul. 25, 2013

(51) Int. Cl.
*C07D 487/22*    (2006.01)

(52) U.S. Cl.
USPC .......................................................... 540/145

(58) Field of Classification Search
CPC .................................................... C07D 487/22
USPC ....................................................... 540/145
See application file for complete search history.

(56) References Cited

PUBLICATIONS

Xue et al. Tetrahedron (2011), 67(33), 6030-6035.*
Armstrong. Neal R.; "Phthalocyanines and porphyrins as materials"; *Journal of Porphyrins and Phthalocyanines*, vol. 4; (2000); pp. 414-417.
Catalano, Maria M., et al; "Control of Reactivity at the Porphyrin Periphery by Metal Ion Co-ordination: a General Method for Specific Nitration at the β-Pyrrolic Position of 5,10,15,20-Tetraarylporphyrins"; *J. Chem. Soc., Chem. Commun.*, (1984) pp. 1535-1536.
Drain, Charles Michael, et al.; "Self-Organized Porphyrinic Materials"; *Chemical Review*, vol. 109; (2009); pp. 1630-1658.
Endo, Masayuki, et al; "Diastereochemically Controlled Porphyrin Dimer Formation on a DNA Duplex Scaffold"; *Journal of. American. Chemical. Society*, 73; (2008); pp. 1106-1112.
Ghosh, Abhik; "Substituent Effects on Valence Ionization Potentials of Free Base Porphyrins: Local Density Functional Calculations and Their Relevance to Electrochemical and Photoelectron Spectroscopic Studies"; *Journal of. American. Chemical. Society*, vol. 117; (1995); pp. 4691-4699.
Gradillas, Ana, et al; "Novel synthesis of 5,10,15,20-tetraarylporphyrins using high-valent transition metal salts"; *J. Chem. Soc., Perkin Trans*; (1995); pp. 2611-2613.
Gündüz Necla, et al; "Titrations in non-aqueous media: potentiometric investigation of symmetrical and unsymmetrical tetra-aryl porphyrins with 4-nitrophenyl and 4-aminophenyl substituents in nitrobenzene solvent"; *Talanta 48*; (1999); pp. 71-79.
Hecht, Stefan, et al.; "Hyperbranched porphyrins—a rapid synthetic approach to multiporphyrin macromolecules"; *Chemical. Communication*; (2000); pp. 313-314.
Jaquinod, L., et al; In The Porphyrin Handbook, Kadish, K. M.; Smith, K. M.; Guilard, R., Eds.; Academic Press: San Diego, (2000); vol. 1; pp. 201H237.
Kruper, Jr, William J., et al; "Regiospecific Aryl Nitration of Meso-Substituted Tetraarylporphyrins: A Simple Route to Bifunctional Porphyrins"; *J. Org. Chem.*, vol. 54, No. 11; (1989); pp. 2753-2756.
Kumar, Devesh, et al; "Theory Favors a Stepwise Mechanism of Porphyrin Degradation by a Ferric Hydroperoxide Model of the Active Species of Heme Oxygenase"; *Journal of American Chemical Society*. 127; (2005); pp. 8204-8213.
Kumar Krishna R., et al; "Supramolecular Multiporphyrin Architecture. Coordination Polymers and Open Networks in Crystals of Tetrakis(4-cyanophenyl)- and Tetrakis(4-nitrophenyl)metalloporphyrin"; *Inorganic Chemistry*, vol. 37, No. 3; (1998); pp. 541-552.
Lane, Benjamin S., et al.; "Metal-Catalyzed Epoxidations of Alkenes with Hydrogen Peroxide"; *Chemical Reviews*, vol. 103, No. 7; (2003); pp. 2457-2473.

(Continued)

*Primary Examiner* — Brian McDowell
(74) *Attorney, Agent, or Firm* — Duane Morris LLP; Siegfried J. W. Ruppert

(57) ABSTRACT

A method of mass production of tetrakis(p-nitrophenyl)porphyrins, by which successful isolation of the barely soluble product from meso-aryl nitration of tetraphenylporphyrin toward a remarkable yield of nearly 90% has been realized by means of a solid phase extraction technique. This is a simpler and more straight forward synthetic method, suitable for production at an industrial scale with lower cost, shorter synthetic time and lower solvent consumption. A preferred species of tetrakis(p-nitrophenyl)porphyrin produced by a subject method is:

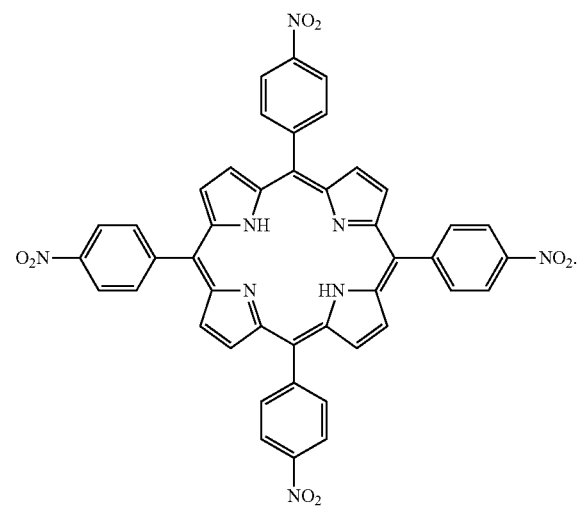

13 Claims, 4 Drawing Sheets

(56) References Cited

PUBLICATIONS

Lindsey Jonathan S., et al.; "Novel synthesis of meso-tetraarylporphyrins using $CF_3SO_2CI$ under aerobic oxidation Rothemund and Adler-Longo Reactions Revisited: Synthesis of Tetraphenylporphyrins under Equilibrium Conditions"; *Journal of Organic Chemistry*, 52; (1987), pp. 827-836.

Lindsey Jonathan S., et al.; "Synthesis of Tetraphrnylporpryrins Under Very Mild Conditions"; *Tetrahedron Letters*, vol. 27, No. 41; (1986); pp. 4969-4970.

Lindsey, Jonathan S., et al; "In the Porphyrin Handbook", Kadish,; Eds.; Academic Press: San Diego, vol. 1 (2000); pp. 45-118.

Liu, Xin Gang, et al.; "Synthesis and Spectroscopic Investigation of Azoporphyrins"; *Chinese Chemical Letters* vol. 16, No. 9; (2005); pp. 1181-1184.

Luguya, Raymond, et al; "Synthesis and reactions of meso-(p-nitrophenyl)porphyrins"; *Tetrahedron 60* (2004) pp. 2757-2763.

Maldotti Andrea, et al.; "Photocatalysis with Organized Systems for the Oxofunctionalization of Hydrocarbons by $O_2$"; *Chemical Reviews*, 102; (2002); pp. 3811-3836.

Meng, Guangzhegn.G, et al; "Porphyrin chemistry pertaining to the design of anti-cancer drugs; part 1, the synthesis of porphyrins containing meso-pyridyl and meso-substituted phenyl functional groups"; *Canadian Journal of Chemistry*. vol. 72; (1994); pp. 1894-1909.

Natale, Corrado Di, et al.; "Chemical sensitivity of porphyrin assemblies"; *Materials Today*, vol. 13, No. 7-8; Jul.-Aug. 2010 pp. 46-52.

Okada, Shinsuke et al.; "Substituent-Control Exciton in J-Aggregates of Protonated Water-Insoluble Porphyrins"; *Journal of American Chemical. Society*, 125; (2003) pp. 2792-2796.

Ostrowski, Stanislaw, et al; "Preparation of meso-Tetraarylporphyrins Nitrated in Two Neighboring Aromatic Rings"; *Synthetic Communications* vol. 33, No. 23; (2003); pp. 4101-4110.

Rothemund, Paul; "A New Porphyrin Synthesis. The Synthesis of Porphin"; *Journal of American Chemical. Society*, 58; (Apr. 1936); pp. 625-627.

Rothemund, Paul; "Porphyrin Studies. III[1] The Structure of the Porphine[2] Ring System"; *Journal of American Chemical. Society*, 61; (Oct. 1939); pp. 2912- 2915.

Rothemund, Paul, et al; "Porphyrin Studies. IV.[1] The Synthesis of α,β,γ,δ-Tetraphenylporphine"; *Journal of American Chemical. Society*, 63; (Jan. 1941) pp. 267-270.

Semeikin, A. S., et al.; "Synthesis of Tetraphenylporphins With Active Groups in the Phenyl Rings."; *13 Chemistry of Heterocyclic Compounds*, vol. 18,; (1983) pp. 1046-1047.

Sharghi, Hashem, et al; "Phosphorus Pentachloride ($PCl_5$) Mediated Synthesis of Tetraarylporphyrins"; *Helvetica Chimica Acta*, vol. 86; (2003); pp. 408-414.

Sharghi, Hashem, et al; "Efficient synthesis of β-hydroxy thiocyanates from epoxides and ammonium thiocyanates using tetraarylporphyrins as new catalysts"; *Journal of Molecular Catalysis A: Chemical 206*; (2003); pp. 53-57.

Sharghi, Hashem, et al; "Novel synthesis of meso-tetraarylporphyrins using $CF_3SO_2CI$ under aerobic oxidation"; *Tetrahedron 60*; (2004); pp. 1863-1868.

Sharma, Pankaz K., "Porphyrin Traps Its Terminator! Concerted and Stepwise Porphyrin Degradation Mechanisms Induced by Heme-Oxygenase and Cytochrome P450"; *Angewandte Chemie International Edition 43*; (2004); pp. 1129-1129.

Song, Li-Cheng, et al; "A Biomimetic Model for the Active Site of Iron-Only Hydrogenases Covalently Bonded to a Porphyrin Photosensitizer"; *Angewantde Chemie International Edition 118* (2006); pp. 1148-1151.

Sun, Licheng, et al; "Novel Biomimetic Models for Photosynthesis: Porphyrins Covalently Linked to Redox-Active Crown Either Quinones"; *Tetrahedron* vol. 51, No. 12; (1995); pp. 3535-3548.

Suslick, Kenneth S., et al.; "The materials chemistry of porphyrins and metalloporphyrins"; *Journal of Porphyrins and Phthalocyanines* vol. 4; (2000); pp. 407-413.

Toganoh, Motoki, et al; "Doubly N-Fused Porphyrin"; *Angewandte Chemie International Edition*, 47; (2008); pp. 8913-8916.

Wathier, Michel, et al.; "Synthesis and Properties of Supramolecular Ionic Networks"; *Journal of American Chemical Society*, vol. 130; (2008); pp. 9648-9649.

Xu, Lan-Lan, et al.; "Covalently Chemical Functionalization of Multi-walled Carbon Nanotubes with Amino Porphyrins"; *ACTA CHIMICA SINICA*, vol. 66, No. 10; (2008); pp. 1228-1234.

Xu, Yanfei, et al.; "A Graphene Hybrid Material Covalently Functionalized with Porphyrin: Synthesis and Optical Limiting Property"; *Advance. Material*, 21; (2009), pp. 1275-1279.

Yamane, Takehiro, et al; "Extreme Rate Acceleration by Axial Thiolate Coordination on the Isomerization of Endoperoxide Catalyzed by Iron Porphyrin"; *Angewandte Chemie International Edition*, 47; (2008); pp. 6438-6440.

Zhang, Xiao-an, et al; "Water-soluble porphyrins as a dual-function molecular imaging platform for MRI and fluorescence zinc sensing"; *Proceeding of The National Academy of Sciences*, vol. 104, No. 26; Jun. 26, 2007 pp. 10780-10785.

\* cited by examiner

Proposed reaction mechanism

METHOD OF MASS PRODUCTION OF TETRAKIS(P-NITROPHENYL)PORPHYRINS

FIELD OF THE INVENTION

The present invention relates to aryl nitration of tetraphenylporphyrin and more particularly, to a method of efficient mass production of tetrakis(p-nitrophenyl)porphyrins.

BACKGROUND OF THE INVENTION

Porphyrin functionalization has long been of great interest in the chemistry community because of the vast potentials and demands for porphyrin derivatives in diverse fields such as materials, supramolecular chemistry, and biomimetic models. Particularly, aryl nitration of meso-tetraphenylporphyrin (abbreviated as $H_2TPP$) has been attractive since $H_2TPP$ is commercially available and the diversity of nitro-group substitution makes it a great synthetic scaffold for sophisticated porphyrin arrays.

More than 20 years ago, Kruper and coworkers reported a simple process to afford a series of highly substituted derivatives based upon electrophilic aromatic substitution of $H_2TPP$ using red fuming nitric acid (Scheme 1). But, this approach, while successfully in producing mono-, di-, and tri-substituted species (compounds 1-4), but no one has been able to obtain the tetra-nitro products (compound 5) in a meaningful yield. Meng et al. later studied the effect of time on the similar nitration reactions and revealed that a trace quantity of 5 (~2% yield with impurities) can be obtained while the reaction time was extended to 2 days. However, further prolonging the reaction time ended up with failure only. The absence or a very low level of 5 observed in the reactions was usually understood as a result of macrocyclic degradation. Recently, a modified process having an improved yield of 2 was described by Ostrowski et al. using yellow fuming nitric acid, but still no 5 can be detected.

Scheme 1. Meso-Aryl nitration of $H_2TPP$

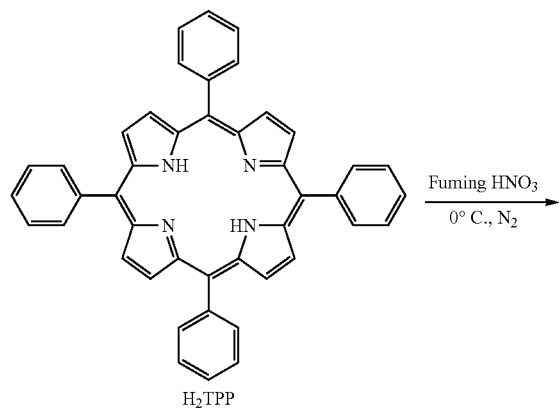

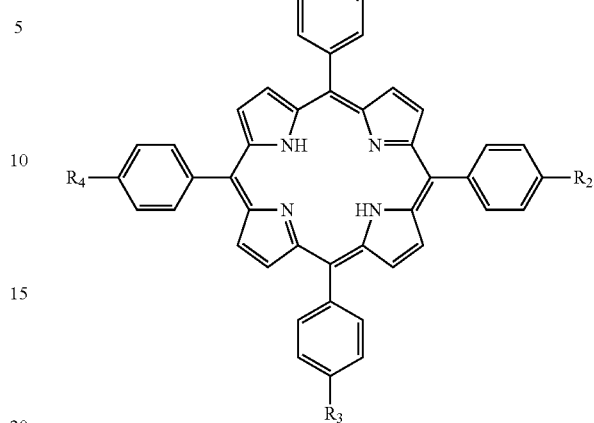

1 $R_1 = NO_2, R_2 = R_3 = R_4 = H$
2 $R_1 = R_2 = NO_2, R_3 = R_4 = H$
3 $R_1 = R_3 = NO_2, R_2 = R_4 = H$
4 $R_1 = R_2 = R_3 = NO_2, R_4 = H$
5 $R_1 = R_2 = R_3 = R_4 = NO_2$ (?)

Prior to the present invention, for synthesis of tetrakis(p-nitro-aryl)porphyrins, the best known methods in the art rely on either Rothermound or Lindsey's condensations. However, the methods usually involve multi-step sequences that require extensive separation steps. The yield of the products is often very low. Due to the vast interest in porphyrin functionalization, there is a long felt need for developing method for efficient production of tetra-derivative of H2TPP in an industrial scale.

SUMMARY OF THE INVENTION

One object of the present invention is to provide a method of efficient production of tetra-derivative of $H_2TPP$ in a single step procedure. Surprisingly, the object is realized by combining the reaction of scheme 1 with a solid phase extraction technique. The method of the present invention leads to a very surprising yield of nearly 90%. In this method, distribution of different nitro-porphyrin components is consequently reassessed with respect to varying acid content in the reactions.

Another object of the present invention is to provide a method for mass production of the tetra-derivative of H2TPP. This object was achieved by a novel process in which silica gel was employed as a substrate to retain the product upon a chromatographic separation and subsequently removed to release the pure product back.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

DETAILED DISCRETION OF THE INVENTION

Figure 1:
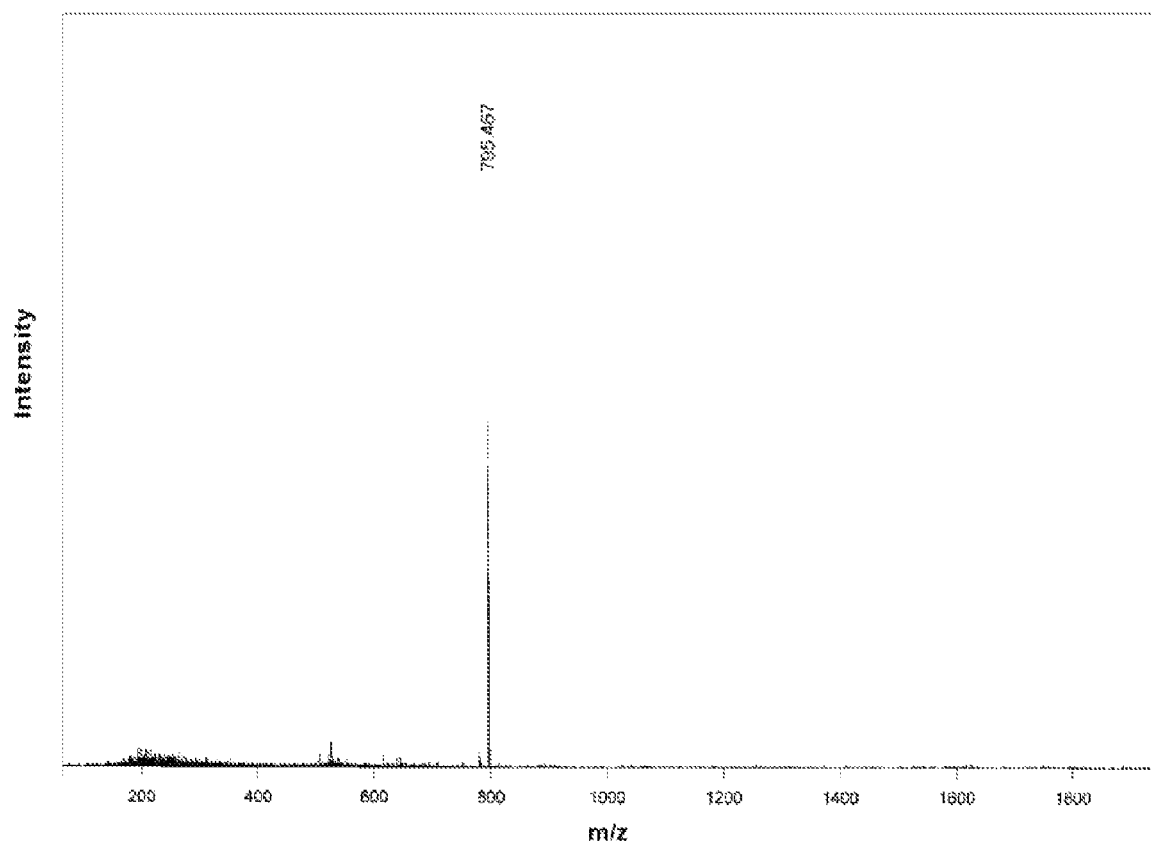
FIG. 1 depicts HRMS spectrum of the insolubles (compound 5) prepared from nitration of $H_2TPP$.
Figure 2:
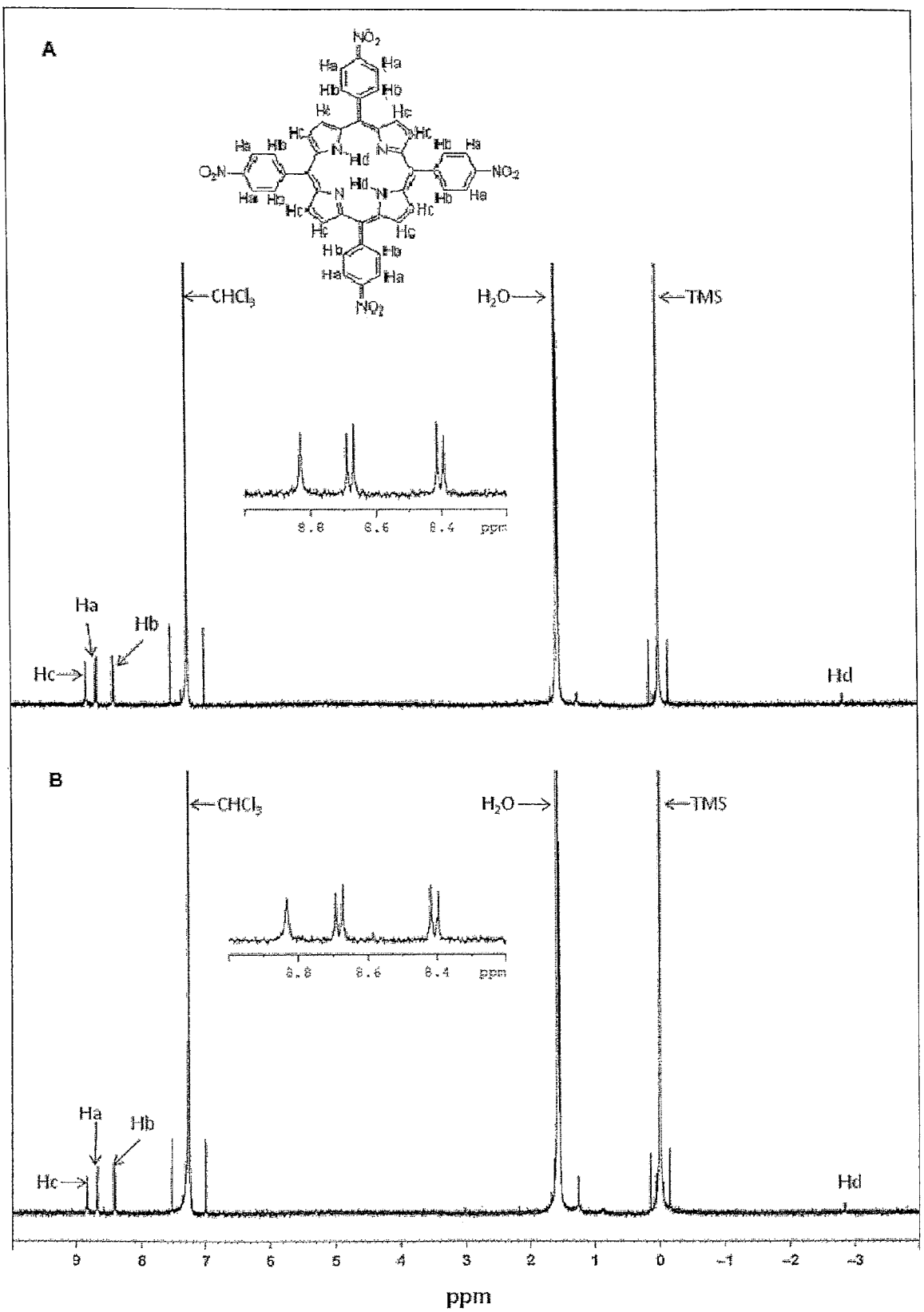
FIG. 2 depicts $^1H$ NMR spectrum of 5 prepared via (A) a nitration reaction and (B) a condensation reaction, respectively, in CDCl$_3$. Chemical shifts δ~7.0 and ~7.5 were attributed to CHCl$_3$ carbon satellite. The shifts near 0 were due to TMS carbon satellite.

The present invention started by simulating a similar nitration experiment on H$_2$TPP according to Kruper (*J. Org. Chem.* 1989, 54, 2753) as shown in scheme 1 above. Pure compounds 1-4 from the crude products were successfully isolated by using column chromatography following standard procedures. However, when adding a large quantity of fuming nitric acid to the reaction, the overall yield of the isolated products went down dramatically. A large amount of dark red insoluble matter was found on the top of the column instead. According to conventional understanding in the art, this could be regarded as the macrocyclic degradation. However, in the present invention, further efforts were made to gain more understanding of the reaction. From this unknown compound, through repetitive elution, a poorly soluble product can be finally extracted and purified. The initial attempt of characterization was made on using FAB-mass spectrometry but unfortunately, there were no obvious identifiable peaks in its spectrum. Although FAB-mass spectrometry was unable to identify the compound, its mass characterization can be realized with the assistance by MALDI-TOF high resolution mass spectrometry. Surprisingly, as shown in FIG. 1, a [M+H]$^+$ ion peak at m/z 795.463 is observed in its spectrum, being a good indicator for the presence of 5 or its isomers (NO$_2$ group(s) located at the porphyrin β-pyrrolic position(s)) when compared to the calculated value (m/z 794.1868) of the M$^+$ ion (C$_{44}$H$_{26}$N$_8$O$_8$). Metallo-H$_2$TPPs under minimal effect of relatively electroneutral metal ions would be nitrated specifically on the meso-position instead of on the β-position (*J. Chem. Soc., Commun.* 1984, 1535). It is therefore highly foreseeable that metal-free H$_2$TPP holds a similar feature that the predominant meso-nitration would afford the corresponding nitro-product, compound 5. In an attempt to collect more supporting information, the compound was subjected to $^1$H NMR measurement after dissolved in deuterochloroform. Since the compound was just sparingly soluble, it was failed to receive any characteristic resonance signals from a normal dissolution sample (only solvent peaks can be identified from the spectrum). However, by bringing the solution to saturation with mild warming, a resolved $^1$H NMR spectrum can be successfully granted. As shown in FIG. 2 (Panel A), although the still very low concentration solution gives rise to a strong carbon satellite effect, all the peaks in concern in the spectrum can be nicely assigned in accord with the theoretical chemical shift values of 5. For example, the protons on the pyrrole rings resonates at 8.83 ppm; the presence of NO$_2$ group attached to the phenyl ring contributes strongly to deshielding effect of the proton nuclei, resulting in resonating at higher δ values, namely ~8.4 and ~8.7 ppm (protons meta and ortho to NO$_2$ group, respectively). Integrating the areas of the resonance peaks also suggests a correct macrocyclic structure of 5 that their peak ratios are in agreement with the molecular structure of each component. The characterization information unambiguously identifies the compound. In addition to the commonplaces for its structural determination, its UV-VIS and fluorescence spectra were measured as well for supplementary reference (Figures S2 and S3 in Supporting information). The results seem to provide the very first evidence that a significant yield of 5 may be harvested from the fundamental nitration reaction of H$_2$TPP using red fuming nitric acid.

Figure 3:
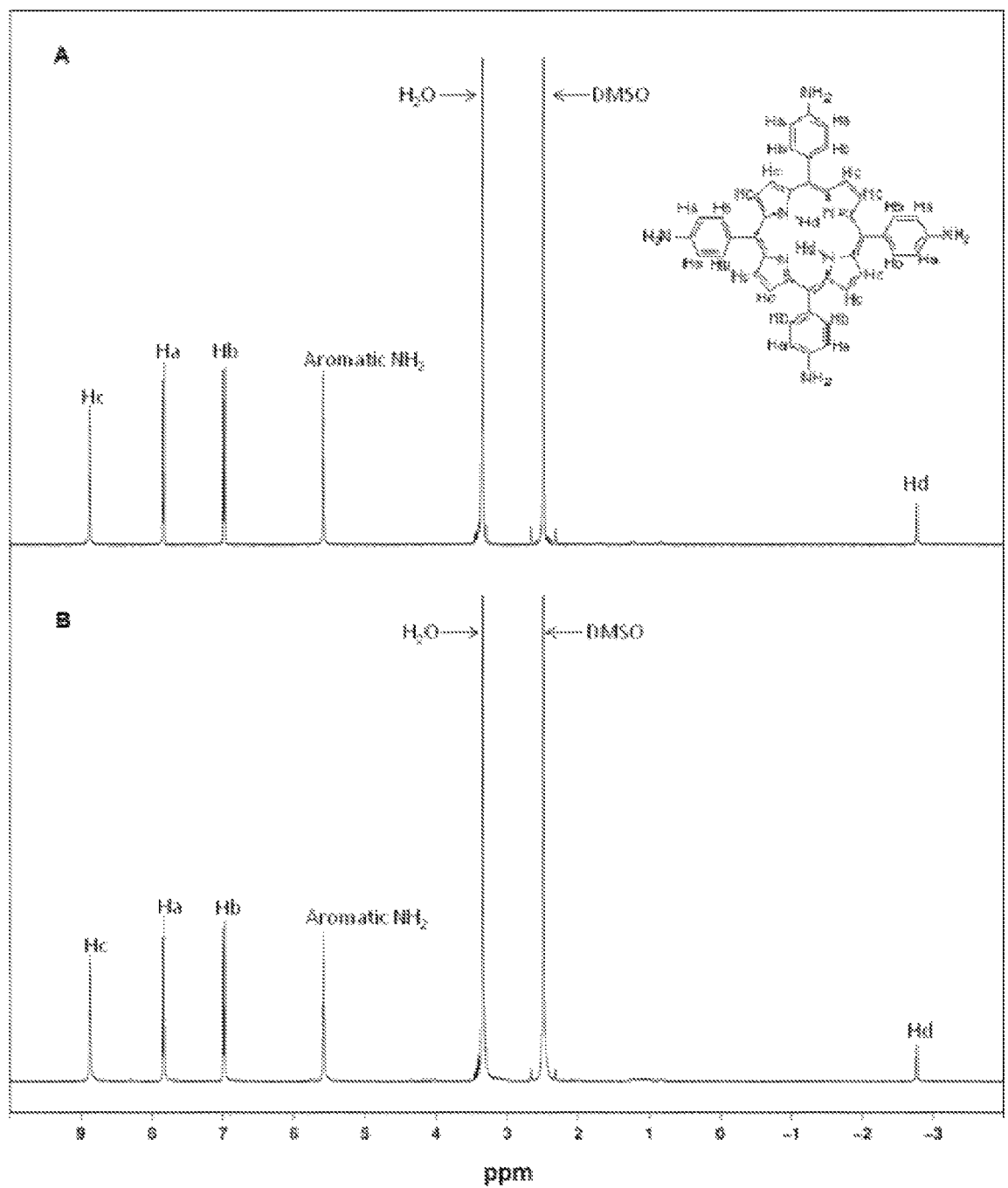
FIG. 3 depicts $^1$H NMR spectra of the reduced products originating from (A) condensation and (B) nitration, respectively, in DMSO-d$_6$.

For assuring the validity of the results, a comparison of the characterization data was made with the reported information, e.g., the NMR records, available from the condensation mode. Unexpectedly, the NMR readings in this study were found only agreeable partially with the published data. To exclude the possibility that mistakes occurred due to the poor solubility of the compound, an additional investigation was carried out. Compound 5 was synthesized through a typical condensation method (*Tetrahedron Lett.* 1986, 27, 4969) and compared it side-by-side with the nitrated compound of the present procedure. From its NMR spectrum (saturated in CDCl$_3$) shown in FIG. 2 (Panel B), it was able to identify the same structural features as those observed in the nitration case. When doing an A-B comparison, a duplicate spectrum is revealed with all the chemical shift data in line with each other (see FIG. 2). It is noted that the two products originating from the different synthetic routes appear to be the same as each other, which is also evidenced by the MALDI-TOF MS analysis done (data not shown). A second characterization supporting identification of compound 5 can be established by converting the NO$_2$ groups, if there exist, to NH$_2$ groups. Herein, under standard SnCl$_2$/HCl conditions (*Chem. Hetrocycle. Compd.* 1982, 18, 1046), the expected corresponding aminoporphyrin, tetra(aminophenyl)porphyrin (H$_2$TAPP) was successfully obtained. As revealed in FIG. 3, the reduced compounds come up with completely resolved $^1$H NMR spectra in deuteroDMSO, which both look indistinguishable to each other. The resonance peaks consent to the molecular structure of H$_2$TAPP, e.g., the protons of its amine (NH$_2$) and aromatic groups at δ~5.6, ~7.0, ~7.9, and ~8.9 ppm, respectively. Furthermore, FAB-mass characterization (data not shown) divulged an equivalent protonated molecular ion peak ([M+H]$^+$) at m/z ~675.0 in each of the spectra, signifying probably the presence of H$_2$TAPP (calcd M+ of H$_2$TAPP=m/z 674.3) in each sample. Such data offer consistent evidence in support of the characteristics of 5 seen in the preceding work of the present invention.

It becomes clear that product 5 is present observably in the nitration process of H$_2$TPP, but it was still not clear to what extent of the nitration occurs and what the product yield is. Due to the poor solubility of 5, the prior purification procedure requires tedious chromatographic elution that makes its large scale synthesis unfeasible. The traditional method by means of Soxhlet apparatus or re-crystallization is not effective too. Accordingly, the present invention designed a special method to realize a large-scale synthesis, in which silica gel was employed as a substrate to retain the product upon a chromatographic separation and subsequently removed to release the pure product back as detailed below. Through this efficient method, high yield and high purity product can be realized along with low solvent consumption. A series of studies concerning the effect of varying the acid content were carried out and it was found that the yield of 5 can be as high as 88% in the reaction. The detailed results are presented in Table 1.

TABLE 1

A series of ratios (acid to H2TPP) was experienced

| Equiv. of fuming nitric acid | Yield$^a$ (%) | | | |
|---|---|---|---|---|
| | 1 | 2&3$^b$ | 4 | 5 |
| 17 | 53 | 5 | 0 | trace |
| 22 | 50 | 8 | 3 | trace |
| 29 | 0 | 28 | 7 | 60 |

TABLE 1-continued

A series of ratios (acid to H2TPP) was experienced

| Equiv. of fuming nitric acid | Yield[a] (%) | | | |
|---|---|---|---|---|
| | 1 | 2&3[b] | 4 | 5 |
| 35 | 0 | 2 | 2 | 87 |
| 40 | 0 | 0 | trace | 88 |

[a]Percentage isolatable yield after silica gel chromatography.
[b]Di-nitrated part contains both the cis and trans isomers, and the cis isomer dominates in all the cases.

Figure 4:
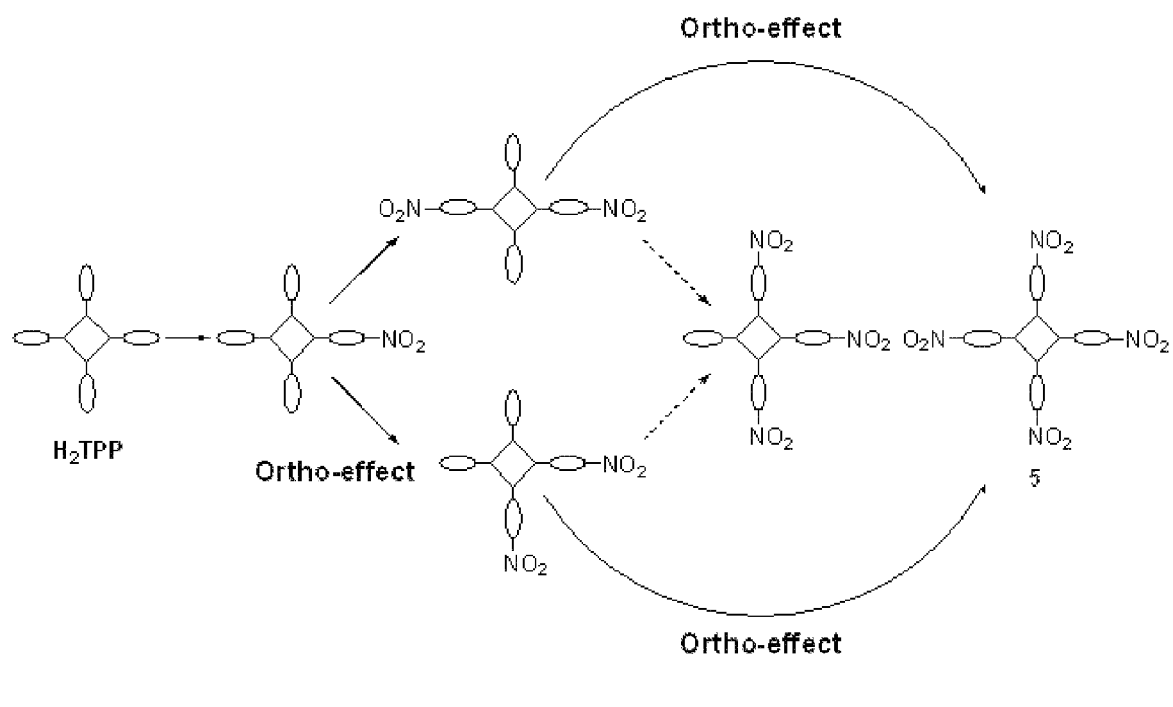
FIG. 4 depicts a proposed reaction mechanism.

Studies on the distribution of different nitro-porphyrin components show more novel results (Table 1). When less fuming nitric acid is added to the $H_2TPP$ solution, mono-substitution is always dominant. However, when acid content increases, there is a shift from mono- to tetra-nitrated product except 4 being hard to be formed all the time. After adding a large amount of acid, tetra-substitution does prevail in the process. The stepwise nitration reaction seems to be following some rules. When $H_2TPP$ is mono-nitrated, further nitration does not occur fairly on other phenyl groups until the acid content is high enough. The neighboring phenyl rings would be more susceptible to electrophilic nitration than the opposite one, leading to more cis isomer available. It is believed that the ortho-effect plays an important role in the reaction mechanism, thus determining the formation of each species. When the di-nitro species (either cis or trans) is further reacted, this effect aids strongly toward a tetra-substituted product. It is then supportive to explain why the tri-nitrated product is always noble under all the reaction conditions and how the major products could be formed. A diagram about the proposed mechanism is illustrated in FIG. 4. The dashed arrows indicate relatively difficult routes to proceed.

Porphyrin degradation is always of a concern in any porphyrin synthesis, although the relevant studies were seldom reported so far. The overall yield of the nitration reaction could not reach 100% and it might be truly due to this problem especially in consideration of the greater reactivity of porphyrin macrocycle compared with phenyl. In the above experiment, TLC analysis on certain raw products showed some other colored spots, which may actually be such impurities from oxidative degradation. Because of this, further effort was made to probe the change of the reaction with relation to some extreme conditions. For example, a bit largely excess of fuming nitric acid was added to a chloroform solution of $H_2TPP$ at room temperature and it was observed that the dark red solution gradually turned into clearly light red. Its UV-VIS spectrum exhibited no typical Soret band absorption at all, suggesting a result of degradation of the porphyrin macrocycle. It was realized that only in an ice-bath under an inert atmosphere was the aryl nitration of $H_2TPP$ largely controlled.

DETAILED DESCRIPTION OF PARTICULAR EMBODIMENTS OF THE INVENTION

Synthetic Procedures and Analytical Data

Synthesis of 5,10,15,20-tetrakis(4-nitrophenyl)-21H,23H-porphyrin (Compound 5)

Via Nitration Method:
A typical experimental procedure (e.g., $H_2TPP$:fuming nitric acid=1:35) is given below. Under an argon atmosphere, red fuming $HNO_3$ (2.4 mL, 56.7 mmol), was added dropwise over a period of 20 min at 0° C. to a 150 mL chloroform solution of $H_2TPP$ (1.0 g, 1.62 mmol). The reaction was kept for 30 mins and then quenched with an aqueous ammonia solution slowly. The organic layer was extracted and evaporated to dryness under reduced pressure. The residual brown powder was washed with boiling water and then subjected to a column separation process. In the process, the powder was first adsorbed onto silica gel followed by an elution with ethyl acetate. The remained dark red band was collected and added into a KOH solution (5% w/v, molar ratio of KOH to silica gel is 2) to remove silica gel. Centrifugation along with repetitive washing with D. I. water afforded the pure product in 87% yield (1.12 g). $^1H$ NMR ($CDCl_3$, 400 MHz, ppm): δ 8.83 (s, 8H, pyrrole alkene protons), 8.68 (d, J=8.0 Hz, 8H, protons ortho to $NO_2$), 8.40 (d, J=8.0 Hz, 8H, protons meta to $NO_2$), −2.83 (s, 2H, protons inside porphyrin macrocycle). LR-MS (FAB, m/z): Calcd $M^+$: 794.2; Found: no obvious identifiable peak. MALDI-TOF (m/z): Calcd $M^+$: 794.1868; Found $[M+H]^+$: 795.467. UV-vis ($CHCl_3$, at saturated concentration, $\lambda_{max}$, nm): 424, 517, 552, 591, 647. Fluorescence (CHCl3, at saturated concentration, nm): $\lambda_{ex}$ 424, $\lambda_{em}$ 652.

Via Condensation of 4-nitrobenzaldehyde and Pyrrole:
The synthesis was based on the condensation of nitrobenzaldehyde with pyrrole according to the method described in the literature (*Tetrahedron Lett.*, 1986, 27, 4969). The product yield was ~4%. $^1H$ NMR ($CDCl_3$, 400 MHz, ppm): δ 8.83 (s, 8H, pyrrole alkene protons), 8.68 (d, J=8.0 Hz, 8H, protons ortho to $NO_2$), 8.41 (d, J=8.0 Hz, 8H, protons meta to $NO_2$), −2.84 (s, 2H, protons inside porphyrin macrocycle). LR-MS (FAB, m/z): Calcd M+ 7942; Found: no identifiable peak. MALDI-TOF (m/z): Calcd $M^+$: 794.1868; Found $[M+H]^+$: 795.1970. UV-vis ($CHCl_3$, at saturated concentration, $\lambda_{max}$, nm): 425, 518, 552, 593, 648. Fluorescence ($CHCl_3$, at saturated concentration, nm): $\lambda_{ex}$ 424, $\lambda_{em}$ 651.

Synthesis of 5,10,15,20-tetrakis(4-aminophenyl)-21H,23H-porphyrin ($H_2TAPP$) Via Reduction of 5

The synthesis followed published procedures (*Chem. Heterocycl. Compd.* 1982, 18, 1046). Its $^1H$ NMR and FAB-mass characterization data is presented herewith.

From Nitration Method:
$^1H$ NMR (DMSO-$d_6$, 400 MHz, ppm): δ8.88 (s, 8H, pyrrole alkene protons), 7.84 (d, 8H, J=5.1 Hz, protons ortho to $NH_2$ groups), 7.00 (d, 8H, J=5.1 Hz, protons meta to $NH_2$ groups), 5.56 (s, 8H, anilinic protons), −2.74 (s, 2H, protons inside porphyrin macrocycle). LR-MS (FAB, m-nitrobenzyl alcohol, m/z): Calcd $M^+$: 674.3; Found $[M+H]^+$: 675.0.

From Condensation Method:
$^1H$ NMR (DMSO-$d_6$, 400 MHz, ppm): δ 8.88 (s, 8H, pyrrole alkene protons), 7.85 (d, 8H, J=5.1 Hz, protons ortho to $NH_2$ groups), 7.00 (d, 8H, J=5.1 Hz, protons meta to $NH_2$ groups), 5.56 (s, 8H, anilinic protons), −2.74 (s, 2H, protons inside porphyrin macrocycle). LR-MS (FAB, m-nitrobenzyl alcohol, m/z): Calcd $M^+$: 674.3; Found $[M+H]^+$: 675.1.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A method of mass production of a tetrakis(p-nitrophenyl)porphyrin, the method comprising the steps of:
    (a) starting a reaction between fuming $HNO_3$ and $H_2TPP$ at a ratio equal or greater than 35:1 to form a tetrakis(p-nitrophenyl)porphyrin in a reaction solution;
    (b) stopping the reaction by adding an ammonia solution to the reaction solution;
    (c) extracting an organic layer from the reaction solution and drying it to afford a residual powder;
    (d) applying the residual powder onto a silica gel;
    (e) eluting the silica gel with a solvent to remove impurities and to leave the tetrakis(p-nitrophenyl)porphyrin adsorbed to the silica gel; and
    (f) obtaining the tetrakis(p-nitrophenyl)porphyrin by releasing it from the silica gel with a base solution.

2. The method according to claim 1, further comprising the step of purification which comprises centrifugation and repetitive washing of the tetrakis(p-nitrophenyl)porphyrin with deionized water.

3. The method according to claim 1, wherein the silica gel is packed into a column.

4. The method according to claim 3, wherein the reaction solution is chloroform.

5. The method according to claim 3, wherein step (a) is for a duration equal or greater than 20 minutes at 0° C.

6. The method according to claim 3, wherein the solvent in step (e) is ethyl acetate.

7. The method according to claim 3, wherein the base solution in step (f) is an alkali.

8. The method according to claim 7, wherein step (e) produces a dark red band in the column and silica gel of the dark red band is collected for further processing in said step (f).

9. The method according to claim 8, wherein the residual powder obtained in step (d) is washed with boiling water before being applied to the silica gel in step (d).

10. The method according to claim 1, wherein in step (e) the silica gel is eluted with more than one solvent.

11. The method according to claim 1, wherein the solvent is selected from the group consisting of ethyl acetate, dichloromethane, chloroform, methanol, and acetone.

12. The method according to claim 10, wherein the solvents are each selected from the group consisting of ethyl acetate, dichloromethane, chloroform, methanol, and acetone.

13. The method according to claim 7, wherein the alkali is KOH.

* * * * *